United States Patent [19]

Albarda

[11] Patent Number: 4,484,576
[45] Date of Patent: Nov. 27, 1984

[54] APPARATUS FOR ADMIXING LIQUID ANESTHETICS AND RESPIRATORY GAS

[75] Inventor: Scato Albarda, Gross Schenkenberg, Fed. Rep. of Germany

[73] Assignee: Drägerwerk Aktiengesellschaft, Fed. Rep. of Germany

[21] Appl. No.: 538,749

[22] Filed: Oct. 3, 1983

Related U.S. Application Data

[62] Division of Ser. No. 368,388, Apr. 14, 1982.

[30] Foreign Application Priority Data

Apr. 29, 1981 [DE] Fed. Rep. of Germany ....... 3116951

[51] Int. Cl.³ ............................................. A61M 16/00
[52] U.S. Cl. ........................... 128/202.22; 128/203.27; 219/273; 219/272; 219/276; 261/130; 261/DIG. 65
[58] Field of Search ...................... 128/200.14, 200.21, 128/203.12, 203.14, 203.25, 203.26, 203.27, 202.22; 219/272, 273, 276; 261/129, 130, DIG. 65

[56] References Cited

U.S. PATENT DOCUMENTS 3,251,361  5/1966  Rusz .................... 128/203.25

FOREIGN PATENT DOCUMENTS 961503  6/1964  United Kingdom ........... 128/203.14

Primary Examiner—Henry J. Recla
Attorney, Agent, or Firm—McGlew and Tuttle

[57] ABSTRACT

An apparatus is disclosed for admixing anesthetic with respiratory gas to be supplied to a patient, which comprises a mixing chamber having an inlet for receiving the liquid anesthesia and the respiratory gas, and an outlet for supplying the mixture. A feed line is provided in the inlet for the liquid anesthesia, with a heat exchanger for equalizing the inlet temperatures of the anesthesia and respiratory gas. Temperature sensors are provided in the inlet and the outlets with a circuit for determining the difference between the temperatures. Without heating of the chamber this difference is proportional to a ratio between the evaporated anesthetic and respiratory gas. With the chamber heated to equate the inlet and outlet temperatures, the amount of heating is proportional to the flow of anesthetic to the chamber.

2 Claims, 2 Drawing Figures

APPARATUS FOR ADMIXING LIQUID ANESTHETICS AND RESPIRATORY GAS

This is a divisonal of application Ser. No. 368,388 filed Apr. 14, 1982.

FIELD AND BACKGROUND OF THE INVENTION

The present invention relates in general to equipment for mixing a vaporizable liquid with a gas flow, and in particular to a new and useful apparatus and method for admixing liquid anesthetics with respiratory gas supplied to a patient.

In medical equipment, in which any failure may lead to life-threatening conditions for the patient, it goes without saying that components or their arrangements are monitored by other components that function independently or that linkages exist in the equipment, which give signals if there are differences between the actual and nominal values. With the signal, visual or auditory alarms are set off and/or automatic corrective measures, such as the switching to reserve assemblies, are initiated. The following known apparatus does not have such control capabilities.

In this known apparatus for admixing liquid anesthetics into the respiratory gas to be supplied to the patient, a gas metering device is arranged in the respiratory gas feed to the patient and one or more injection pumps for the anesthetics are connected. It further comprises one or more cylinders with plungers that are adjustable in their immersion depth, in which the anesthetic supply ends. The immersion depth is dependent on the quantity of respiratory gas flowing to the patient in a manner which is controlled via levers. The anesthetic displaced from the cylinders by the immersion of the plungers is introduced or injected into the respiratory gas stream. The lever control can be effected by a double piston moving in a cylinder, the piston being moved alternately by the respiratory gas flowing in from the patient. This known apparatus is operated by the pressure of the respiratory gas. Besides the crucial disadvantage pointed out above, of lacking control, it must be noted also that the friction forces possibly varying at the gas double pistons and in the lever system must be overcome. Owing to this, then, the gas quantity per stroke and hence the anesthetic concentration changes, so that the concentration is thus friction dependent. The dry cylinder seals used are subject to heavy wear as well. (See German Pat. No. 12 71 902).

SUMMARY OF THE INVENTION

It is the object of the present invention to provide an apparatus for admixing liquid anesthetics into respiratory gas to be supplied to a patient which, in a simple and functioning arrangement, fulfills the requirements of safe monitoring by the operating personnel and/or the automatic initiation of corrective measures.

Accordingly, an object of the invention is to provide an apparatus for admixing a vaporizable liquid with a gas comprising, a housing defining a mixing chamber, an inlet conduit connected to the housing for a flow of gas to the chamber, a liquid feed line in the inlet conduit for supplying liquid to the chamber, the feed line including a heat exchanger for equalizing the inlet temperature of the liquid with the inlet temperature of the gas in the inlet conduit, a first temperature in the inlet conduit sensing the inlet temperature, an outlet conduit connected to the housing for a flow of vaporized liquid plus gas mixture from the chamber, a second temperature sensor in the outlet conduit for sensing the outlet temperature of the mixture, liquid supply means connected to the feed line and gas supply means connected to the inlet conduit for controlling the flow of liquid and gas respectively to the chamber, nominal value set means connected to the liquid and gas supply means for controlling the supply means to supply liquid and gas at selected levels, and temperature difference measuring means connected to the first and second temperature sensors and to at least one of the liquid and gas supply means for measuring a difference between the inlet and outlet temperatures, which difference is proportional to the ratio between vaporized liquid concentration and gas concentration.

A further object of the invention is to provide such an apparatus which includes heating means connected to the housing for heating the chamber by a selected amount, the temperature difference measuring circuit means including a temperature difference measuring circuit and a control and evaluation circuit, a switch connected to the heating means and controllable by the control and evaluation circuit, the temperature difference measuring circuit connected to the switch for applying power to the heating means proportional to the difference between the inlet and outlet temperatures to reduce the difference to zero, the amount of power supplied to the heating means being a measure of the flow of anesthetic to the housing.

A still further object of the invention is to provide such an apparatus wherein the control and evaluation circuit includes indicators for indicating a deviation of the actual liquid and gas flow from the nominal values therefor.

The inventive arrangement offers the possibility of control both of the liquid, here the anesthetic, and of the gas, here the respiratory gas. In a first measuring mode (a) for monitoring the anesthetic flow, it is ascertained if the actual value of the heat absorbed for the vaporization of the liquid concords with the nominal value. If not, that is, if the respective warning lamp lights up, this indicates either a pump malfunction, that is the pump did not convey the nominal volume, or that the operator did not replenesh the anesthetic liquid. In the second measuring mode (b) the cooling of the gas-vapor mixture is compared with a nominal value. If they are not identical, again the respective warning lamp lights up, the anesthetic concentration, i.e., the concentration of the vaporizing anesthetic in the respiratory gas, is not correct. This may be due, if the nominal value (a) is respected, either to deviations of the respiratory gas flow, e.g. through failure of the respiratory gas valve, or because the gas is the wrong specific heat, that is, the wrong gas is being supplied.

The apparatus according to the invention proves to be a simple, safe and yet informative device.

The inventive principle of measurement can in addition be used generally wherever vaporizing liquids are to be admixed to a gas stream in a defined manner. For example, the admixture of vaporizing fuels to the primary air of an Otto engine or the adjustment of a planned relative moisture in a room or in respiratory air, can be controlled.

The quantity of heat required for temperature equalization between the liquid and the gas stream is always small as compared with the quantity of heat required for evaporation. For applications where the requirements of accuracy are lower, the temperature equalization and the joint admission with heat exchanger provided for that purpose, may therefore be dispensed with in the interest of a simpler construction, without going outside the scope of the invention.

The various features of novelty which charcterize the invention are point out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
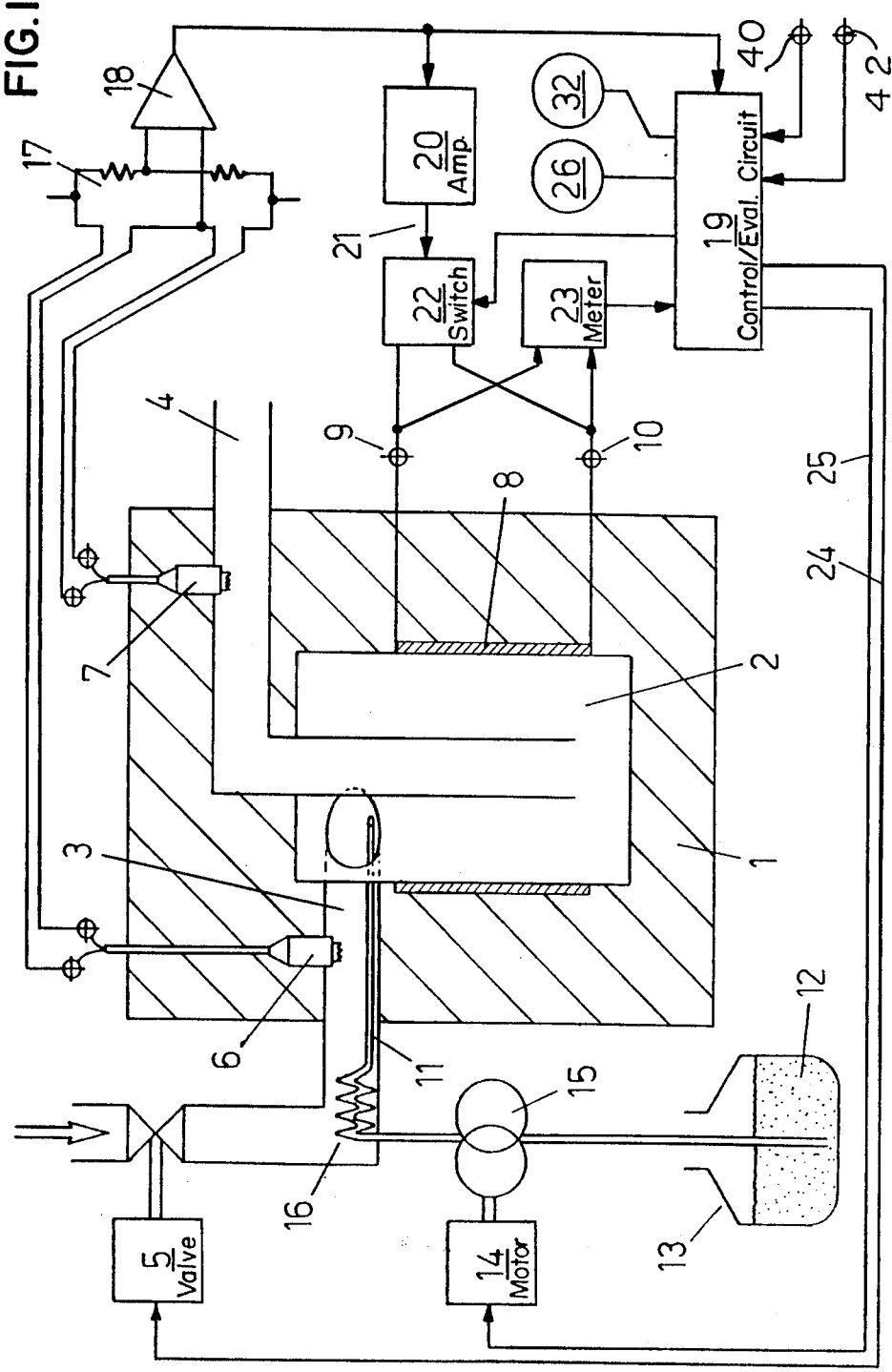
FIG. 1 is a schematic block diagram of the invention which shows an apparatus for monitoring, (a) the anesthetic flow and, (b) the respiratory gas flow.
Figure 2:
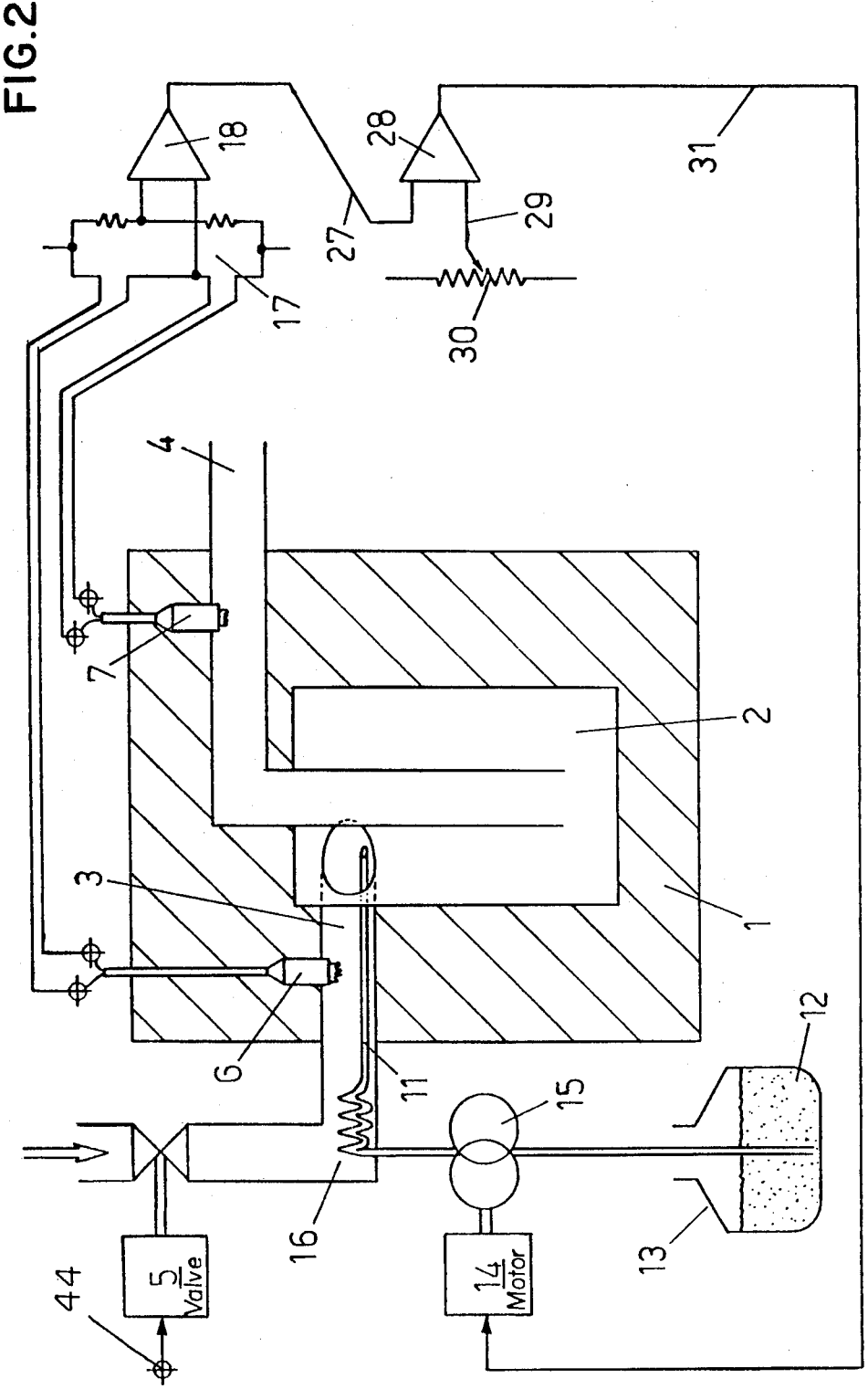
FIG. 2 is a similar view of an apparatus for maintaining the anesthetic concentration, according to the invention.

Referring to the drawings in particular, the invention embodied therein in FIGS. 1 and 2 comprise an apparatus for admixing liquid with gas, in particular liquid anesthetics with respiratory gas, to control liquid and gas supply means so that they supply nominal values of the liquid and gas flow rate to a mixing chamber.

A heat insulating housing 1 contains a measuring chamber 2 with an inlet 3 and an outlet 4. An electrically controlled respiratory gas valve 5 and an inlet temperature sensor 6 are mounted in inlet 3. A temperature sensor 7 is mounted in outlet 4. The wall of the measuring chamber 2 contains, as heating means, an electric heating element 8 with leads 9,10.

A feed line 11 for liquid anesthetic 12 ends in the inlet 3. It goes from an anesthetic vessel 13 via a proportioning pump 15 driven by a motor 14 to approximately the tangential feed of inlet 3 into the measuring chamber 2. Before the inlet temperature sensor 6, the feed line 11 includes a heat exchanger 16 in the form of coils.

The respiratory gas is supplied at inlet 3 and thence enters the (cylindrical) measuring chamber 2 tangentially. In the resulting cyclone type flow the liquid anesthetic 12, supplied through line 11, vaporizes and in so doing becomes mixed uniformly with the respiratory gas. Compensated by the heat exchanger 16, the respiratory gas and the liquid anesthetic 12 have, before entering the measuring chamber 2, the same temperature, which is measured by the inlet temperature sensor 6. The outlet temperature sensor 7 measures the temperature of the issuing anesthetic respiratory gas mixture. The temperature sensors 6, 7 are resistance sensors and form part of a bridge circuit 17 whose output (difference) signal is sent via an amplifier 18, firstly to a control and evaluating circuit 19 and secondly to an amplifier 20. The output 21 of amplifier 20 is connected to the heating element or system 8 via a switch 22 which is controlled by the control and evaluating circuit 19. Amplifier 20 produces a current for heating element 8 which is proportional to the difference signal from amplifier 18. A wattmeter 23 is connected by its inputs with the leads 9, 10 of the heating system 8 and by its output with the control and evaluating circuit 19.

When respiratory gas provided by inlet 3 and liquid anesthetic provided by line 11 enter chamber 2 they swirl around violently and the anesthetic vaporizes. Since heat must be added to a liquid when it is converted from a liquid phase to a vapor phase, the anesthetic, as it vaporizes, absorbs heat from its surroundings. This causes a temperature drop between the inlet temperature sensed at sensor 6 and the outlet temperature of the vapor mixture in line 4 as sensed by sensor 7. This temperature drop can be used in two ways according to the invention, the first way, identified as mode (a) below, measures the absolute amount of an anesthetic being added to the gas, and the second way, identified as mode (b) to determine the concentration of anesthetic in the respiratory gas, that is the amount of anesthetic per unit amount of gas. This second mode of use for the temperature difference does not give an absolute amount of the anesthetic in the gas, but the ratio in amounts of anesthetic to gas.

The control and evaluating circuit 19 has a set point for the anesthetic flow and a set point for the respiratory gas flow (lines 40 and 42). Its control output 24 is connected with the respiratory gas valve 5 and its control output 25 with the motor 14 of the proportioning pump 15. It further has a warning lamp 32 for the anesthetic flow and a warning lamp 26 for the respiratory gas flow. By periodic switching its operational mode, the control and evaluating circuit 19 effects several controls:

Mode (a) For monitoring the anesthetic flow, switch 22 is closed and thus the heating system 8 is activated in a controlled manner until there results, at the temperature sensors 6, 7 a temperature difference of "zero" and hence at the amplifier 20 the voltage difference "zero". In this state the amount of heating power supplied just covers the heat of evaporation of the quantity of anesthetic supplied to chamber 2, per unit time. External factors are excluded by the heat insulation of the housing 1. This condition is independent of the respiratory gas flow rate, as the quantity thereof, composition and temperature at the inlet 3 and outlet 4 are the same. The required heating power is a measure of the anesthetic flow. The amount of heating power is determined by the wattmeter 23 and is compared with the set nominal value in the control and evaluating circuit 19. In case of deviation, the warning lamp 32 lights up.

Mode (b) For monitoring the respiratory gas flow, switch 22 is opened by the control and evaluating circuit 19, so that the heating system 8 is turned off (disconnected from amplifier 20). The signal of amplifier 18 is now proportional to the occurring temperature difference at the temperature sensors 6,7, which despends on the ratio between evaporated anesthetic and respiratory gas, that is, the concentration. The signal of amplifier 18 is thus a measure of the concentration of the evaporated anesthetic in the respiratory gas. The validity of this measurement is evidently dependent upon a complete evaporation of liquid anesthetic, which requires a sufficiently high temperature at the outflow (sensor 7). Preheating of the incoming gas flow may be required in some cases. The value of the quotient, anesthetic flow to anesthetic concentration is then a measure of the rate of flow of respiratory gas.

This quotient is formed in the control and evaluating circuit 19 and is compared with the set nominal value for the respiratory gas flow. In case of deviation, the warning lamp 26 lights up. The alarm which is set off, can be used to readjust the setting of the nominal values.

The indication of the warning lamps 26, 32 remains, so as to call attention to the fault or error. The structure of circuit 19 to achieve the invention, is within the knowledge of the art. The circuit according to FIG. 2 is a modification which assures maintenance of the anesthetic concentration at varying respiratory gas flow by automatic regulation of the anesthetic flow. Here the output signal of amplifier 18, corrresponding to the anesthetic concentration (note there is no heater) is supplied to the input 27 of an amplifier 28, to whose other input 29 a nominal value is supplied via potentiometer or setting means 30 for the desired anesthetic concentration. The output of amplifier 28 controls, via a control line 31, the motor 14 of the proportioning pump 15 and thereby maintains the set anesthetic concentration. Respiratory gas flow is set at a nominal value over adjustment 44.

While specific embodiments of the invention have been shown and described in detail to illustrate the application of the principles of the invention, it will be understood that the invention may be embodied otherwise without departing from such princples.

What is claimed is:

1. A method of controlling the flow of liquid anesthetic and respiratory gas to a mixing chamber having an inlet and an outlet for mixing vaporized liquid anesthetic with the respiratory gas, comprising:

providing a flow of respiratory gas to a mixing chamber;

providing a flow of liquid anesthetic to said mixing chamber, causing said flow of liquid anesthetic to admix with said flow of respiratory gas to an extent to atomize and evaporate the liquid anesthetic;

establishing a heat exchange relationship between the respiratory gas and liquid anesthetic before they enter the mixing chamber for equating the inlet temperatures thereof;

sensing a difference between the inlet temperature and an outlet temperature of the evaporated liquid anesthetic plus gas mixture to and from the chamber which difference is a result of the heat of evaporization of the liquid anesthetic;

using the temperature difference to control the flow of liquid anesthetic to the chamber, the temperature difference being directly proportional to a ratio in concentrations between the evaporated anesthetic and the respiratory gas.

2. A method of measuring the flow of liquid anesthetic to a mixing chamber having an inlet and an outlet for mixing vaporized liquid anesthetic with the respiratory gas to form a mixture, comprising:

providing a flow of respiratory gas to a mixing chamber;

providing a flow of liquid anesthetic to said mixing chamber;

causing said flow of liquid anesthetic to admix with said flow of respiratory gas to an extent to atomize and evaporate the liquid anesthetic;

selecting a nominal valve for the liquid anesthetic flow into the chamber;

establishing a heat exchange relationship between the respiratory gas and the liquid anesthetic before the gas and anesthetic enter the mixing chamber to form the mixture to cause the temperatures of the respiratory gas and liquid anesthetic to become equal to an inlet temperature;

sensing the inlet temperature;

sensing an outlet temperature of the mixture from the chamber;

measuring the difference between the inlet temperature and the outlet temperature to obtain a difference value and converting said difference value to a power value;

amplifying the power value for powering a heater, which power value is directly proportional to the difference value;

heating the chamber using a heater activated with the amplified power value over a period of time until the inlet temperature is made to equal the outlet temperature so that the difference value falls to zero and therefore, the power value falls to zero;

measuring the power value over the period of time to obtain a value corresponding to the total amount of energy supplied to the heater, the total amount of energy being directly proportional to the liquid anesthetic flow into the chamber; and comparing the measured power valve with the selected nominal valve and activating an alarm if the measured valve is not equal to the selected nominal valve.

* * * * *